United States Patent [19]

Merz et al.

[11] Patent Number: 4,473,573

[45] Date of Patent: Sep. 25, 1984

[54] N-(2-METHOXYETHYL)-NOROXYMORPHONE AND PHARMACEUTICAL COMPOSITIONS FOR RELIEVING PAIN CONTAINING SAME

[75] Inventors: Herbert Merz, Ingelheim; Adolf Langbein, Gau-Algesheim; Klaus Stockhaus, Bingen, all of Fed. Rep. of Germany

[73] Assignee: Boehringer Ingelheim KG, Ingelheim am Rhein, Fed. Rep. of Germany

[21] Appl. No.: 495,513

[22] Filed: May 17, 1983

[30] Foreign Application Priority Data

Jun. 3, 1982 [DE] Fed. Rep. of Germany ....... 3220831

[51] Int. Cl.³ .................. A61K 31/485; C07D 489/08
[52] U.S. Cl. ....................................... 424/260; 546/45
[58] Field of Search .................... 546/44, 45; 424/260

[56] References Cited

U.S. PATENT DOCUMENTS 3,332,950  7/1967  Blumberg et al. .................... 546/45

OTHER PUBLICATIONS

Clark, et al., J. Am. Chem. Soc., vol. 75, pp. 4963–4967 (1953).
Winter, et al., Arc. Int. Pharmacodyn., vol. 110, No. 2–3, pp. 186–202 (1957).

Primary Examiner—Donald G. Daus
Assistant Examiner—Diana G. Rivers
Attorney, Agent, or Firm—Hammond & Littell, Weissenberger & Dippert

[57] ABSTRACT

The invention relates to N-(2-methoxyethyl)-noroxymorphone and pharmacologically acceptable acid addition salts thereof. These compounds are analgesically effective and can be used for controlling pain.

3 Claims, No Drawings

N-(2-METHOXYETHYL)-NOROXYMORPHONE AND PHARMACEUTICAL COMPOSITIONS FOR RELIEVING PAIN CONTAINING SAME

FIELD OF THE INVENTION

This invention relates to N-(2-methoxyethyl)-noroxymorphone. More particularly, this invention relates to N-(2-methoxyethyl)-noroxymorphone and pharmacologically acceptable acid addition salts thereof, the preparation thereof, and pharmaceutical compositions containing same.

DETAILED DESCRIPTION OF THE INVENTION

Applicants' invention relates to N-(2-methoxyethyl)-noroxymorphone of the formula

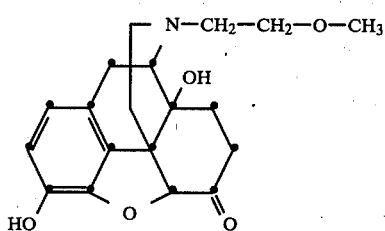
(I)

and pharmacologically acceptable acid addition salts thereof with inorganic or organic acids, pharmaceutical compositions containing them, and procedures for the preparation thereof. The compound of Formula I and said acid addition salts thereof (hereinafter referred to as "the compounds of formula I") are useful as analgesics.

N-Substituted noroxymorphone compounds are known. For example, compounds of the formula

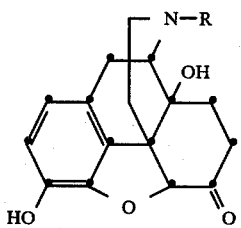
(II)

wherein R represents (IIa) $CH_3$, (IIb) $CH_2$—$CH$=$CH_2$, or (IIc) $CH_2$—$\Delta$ are disclosed in U.S. Pat. Nos. 2,806,033, 3,254,088, and 3,332,950, respectively. These compounds are known as oxymorphone, naloxone, and naltrexone, respectively. The novel compounds of the formula

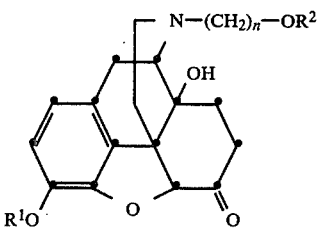
(III)

wherein (IIIa) $R^1$=H, $R^2$=$C_2H_5$, and n=2; (IIIb) $R^1$=$CH_3$, $R^2$=$CH_3$, and n=2; (IIIc) $R^1$=$CH_3$, $R^2$=$C_2H_5$, and n=2; and (IIId) $R^1$=H, $R^2$=$CH_3$, and n=3, were prepared for comparison pruposes.

The compounds of Formula I may be prepared as follows:

Method A

Noroxymorphone of the formula

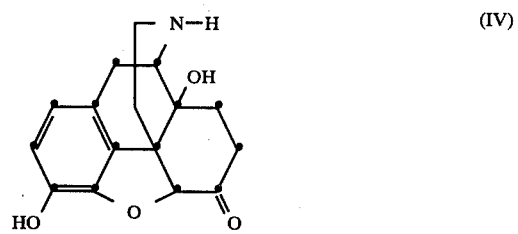
(IV)

is alkylated with 2-methoxyethyl-halide of the formula $$X-(CH_2)_2-OCH_3 \qquad (V)$$

wherein X represents a chlorine, bromine, or iodine atom. Either the calculated quantity or a slight excess of the alkylation agent of Formula V is used, and the work is preferably done in the presence of acid-binding substances such as triethylamine, dicyclohexylethylamine, sodium carbonate, potassium carbonate, calcium oxide, or, especially, sodium bicarbonate. It is advantageous to carry out the reaction in an inert solvent, such as, chloroform, methylene chloride, benzene, acetone, dioxane, tetrahydrofuran, or dimethylformamide. It is preferred to use mixtures of dimethylformamide and tetrahydrofuran.

The reaction temperature may vary within wide limits. The temperatures used are preferably between ambient temperature and the boiling point of the solvent used. After the reaction, the reaction products are isolated, purified, and crystallized using known methods and optionally converted into suitable acid addition compounds.

Method B

A compound of the formula

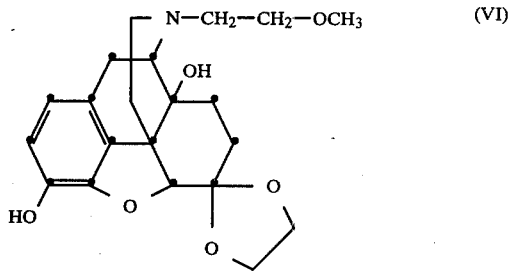
(VI)

is reacted with dilute acid to provide ketal splitting.

The noroxymorphone of Formula IV is normally obtained from thebaine in sterically uniform form. The starting compound of Formula VI required for Method B can be obtained from noroxymorphone by ketalization with glycol in the presence of acid, acylation of the ketal of Formula VII with methoxyacetic acid chloride to form the acyl derivative of Formula VIII, and subsequent reduction with lithium aluminium hydride according to the following reaction scheme:

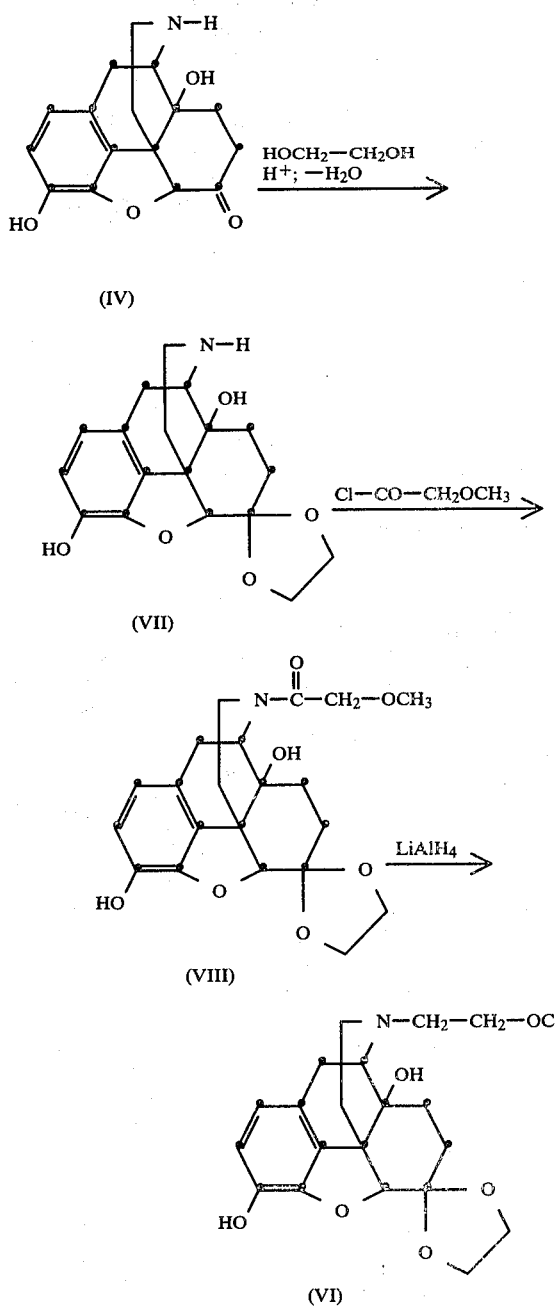

The compound of Formula I is a base and may be converted into pharmacologically acceptable acid addition salts thereof in conventional manner. Acids suitable for salt formation include, for example, hydrochloric, hydrobromic, hydriodic, hydrofluoric, sulfuric, phosphoric, nitric, acetic, propionic, butyric, valeric, pivalic, caproic, oxalic, malonic, succinic, maleic, fumaric, lactic, tartaric, citric, malic, benzoic, phthalic, cinnamic, salicyclic, and ascorbic acid, 8-chlorotheophylline, methanesulfonic acid, and ethanephosphonic acid, and the like.

The compounds of Formula I have a therapeutically useful effect on the central nervous system and can be used as non-addictive analgesics, i.e., pain-relieving agents. The compound of Formula I is an opioid agonist-antagonist with a non-morphine-like activity profile not found in other substances. Some pharmacological data which serve to distinguish it over related substances are discussed below.

The strong analgesic property can be demonstrated in the writhing test. In this test, the compound of Formula I, having an ED$_{50}$ of 0.013 mg/kg s. c., is about 36 times stronger than morphine, which has an ED$_{50}$ of 0.47 mg/kg s. c., or about 2.5 times stronger than the structurally closely related analgesic oxymorphone of Formula IIa (ED$_{50}$=0.032 mg/kg s. c.).

The non-morphine-like activity profile can be recognized from the absence of typical side effects produced by opiates. In contrast to the comparison substances mentioned above, namely, morphone, oxymorphone and other opiates, the hydrochloride of the compound of Formula I does not show, for example, either the Straub morphine tail phenomenon or so-called compulsive circular motion. The difference between the hydrochloride of the compound of Formula I and the opiates, which have a high potential for misuse, can also be seen in that the substance is not capable of relieving the withdrawal symptoms occuring in morphine-dependent monkeys after the morphine has been withdrawn. In this experiment, the hydrochloride of the compound of Formula I behaves rather as an antagonist in that it aggravates the withdrawal symptoms.

The morphine-antagonistic component can be demonstrated in the Haffner test by the reversal of the analgesia produced by morphine. The compound of Formula I, having an AD$_{50}$ of 0.3 mg/kg s. c., has about 1/10 of the antagonistic activity of the structurally closely related comparison substance naloxone of Formula IIb (AD$_{50}$=0.03 mg/kg s. c.). In morphine-dependent monkeys there is found to be increased sensitivity of morphine antagonists which trigger withdrawal symptoms, dependent upon dosage. According to the experiment, the compound of Formula I is as strong as naloxone. Unlike the compound of Formula I, naloxone and the second substance naltrexone of Formula IIc have no analgesic activity but are so-called "pure antagonists."

One particular advantage of the compound of Formula I over other opiate-type analgesics, agonists, and agonist-antagonists is its unusually high therapeutic range, which is 103,846 with an LD$_{50}$ of 1350 mg/kg s. c. in mice, based upon the effect in the writhing test. The comparison values are 1600 for the standard analgesic morphine and 169 for the agonist-antagonist pentazocine which is used therapeutically as an analgesic.

Another advantage of the compound of Formula I over newer substances, not yet used therapeutically, selected from the opioid kappa agonists of the benzomorphane series, to which a high therapeutic range is also ascribed (for example, 1800 for ethylketazocine), is the absence of any strong sedation. This can be recognized in the comparison substances as an inhibition of locomotion in mice in or near the therapeutic dosage range. In the compound of Formula I, however, this effect was not observed in the range tested up to very high doses of 100 mg/kg.

The independent opioid activity profile of the compound of Formula I is obtained from studies on test organs, such as the vas deferens of the mouse and the guinea pig ileum and receptor preparations.

Systematic modification of the structure of Formula I has always resulted in substances with substantially less favorable properties. The corresponding N-(2-ethoxyethyl) compound of Formula IIIa, for example, has only 1/20 of the activity of the compound of Formula I, while the N-(3-methoxypropyl) compound of Formula IIId has only 1/25. Moreover, the compound of Formula IIId is similar to morphine in its effects. Etherification of the phenolic hydroxy group to yield the structures of Formulas IIIb and IIIc reduces the activity, for example, to 1/84 in the case of the compound of Formula IIIb.

The compounds of Formula I may be administered by enteral or parenteral route. The dosage for enteral and parenteral administration is from about 0.5 to 100 mg (from about 0.0007 to 1.3 mg/kg), preferably from about 1 to 20 mg (from about 0.013 to 0.27 mg/kg). The compounds of Formula I may also be combined with other pain-relieving agents or with active substances of other kinds such as sedatives, tranquilizers, or hypnotics. Suitable galenic forms for administration include, for example, tablets, capsules, suppositories, solutions, suspensions, powders, and emulsions. These may be prepared using the galenic excipients and carriers, disintegrants, lubricants, or substances for obtaining delayed release which are conventionally used. These galenic preparations may be made in the usual way using known methods of production.

The tablets may consist of several layers. Similarly, coated tablets may be prepared by taking cores produced analogously to the tablets and coating them with agents conventionally used for coating tablets, such as polyvinylpyrrolidone, shellac, gum arabic, talc, titanium dioxide, or sugar.

To obtain delayed release or to avoid incompatibilities, the core may also consist of several layers. Similarly, the tablet coating may also be made up of several layers to obtain delayed release, and the excipients mentioned above for the tablets may be used.

Syrups of the active substances or combinations of active substances according to the invention may additionally contain a sweetener such as saccharin, cyclamate, glycerine, or sugar or a flavor-improving agent, for example, a flavoring such as vanillin or orange extract. They may also contain suspension adjuvants or thickeners such as sodium carboxymethyl cellulose, wetting agents such as condensation products of fatty alcohols with ethylene oxide, or preservatives such as p-hydroxybenzoates.

Injection solutions are prepared in conventional manner, such as, by the addition of preservatives such as p-hydroxybenzoates or stabilizers such as complexones, and then sealed in injection vials or ampules.

Capsules containing the active substances or combinations of active substances may, for example, be prepared by mixing the active substances with inert carriers such as lactose or sorbitol and then encapsulating them in gelatine capsules.

Suitable suppositories may be prepared, for example, by mixing the active substances or combinations of active substances intended for this purpose with conventional carriers such as neutral facts or polyethylene glycol or the derivatives thereof.

The following examples are intended to illustrate the invention and should not be construed as limiting it thereto.

EXAMPLES

PREPARATION EXAMPLES

EXAMPLE 1

N-(2-Methoxyethyl)-noroxymorphone (Method A)

Quantities of 3.24 gm (0.01 mol) of noroxymorphone hydrochloride, 2.6 gm (0.03 mol) of sodium bicarbonate, and 1.52 gm (0.011 mol) of 2-methoxyethylbromide were stirred vigorously in 35 ml of dimethylformamide for 24 hours at 60° C. The mixture was then concentrated by evaporation in vacuo, and the residue was shaken with 45 ml of methylene chloride, 5 ml of isopropanol, and 20 ml of water. The organic phase was washed three times, each time with 20 ml of water, dried with sodium sulfate, and concentrated by evaporation in vacuo. The crude product (3.3 gm) was purified by chromatography on silica gel, methanol/chloroform/conc. ammonia (90:10:0.5) being used as eluant. The fractions containing the pure substance were concentrated by evaporation. The residue (2.7 gm) crystallized when treated with 20 ml of diethyl ether. The crystal suspension was kept overnight in a refrigerator, subjected to suction filtration, washed with a small amount of ether, and dried at 70° C. An amount of 1.7 gm (49.3% of theory) of N-(methoxyethyl)-noroxymorphone, melting point 164–168° C., was obtained. After recrystallization from methanol/water (2:1), the substance melted at 170–173° C.

EXAMPLE 2

N-(2-Methoxethyl)-noroxymorphone (Method B)

(a) N-Methoxyacetyl-noroxymorphone-ethylene ketal

A solution of 47.8 gm (0.44 mol) of methoxyacetylchloride in 331 ml of absolute methylene chloride was added dropwise to a vigorously stirred solution/suspension of 66.2 gm (0.2 mol) of noroxymorphone-ethylene ketal in 662 ml of absolute methylene chloride and 80 ml of triethylamine, at a reaction temperature of 10° C., over a period of about two hours, while the mixture was cooled with ice. A clear solution was obtained which was refluxed for one hour. After it cooled, the methylene chloride solution was washed three times with water, dried with sodium sulfate, and concentrated by evaporation in the rotary evaporator, finally in vacuo. The residue was taken up in 100 ml of toluene, and the solution was evaporated again. The crystalline residue (91.2 gm) consisted of N-methoxyacetylnoroxymorphone-ethylene ketal, which was reacted further without intermediate purification.

(b) N-(2-Methoxyethyl)-noroxymorphone ethylene ketal

The evaporation residue described in step (a) was dissolved in 1400 ml of absolute tetrahydrofuran, with heating. After cooling to 25° to 30° C., the solution was added dropwise, over a period of four hours, to a vigorously stirred suspension of 24.0 gm (0.63 mol) of lithium aluminum hydride in 600 ml of absolute tetrahydrofuran. The reaction mixture was cooled to ensure that the reaction temperature did not rise above 30° to 35° C. Subsequently, the reaction mixture was refluxed for two hours. It was then cooled, and 300 ml of water were added dropwise, at 0° to 5° C., with cooling and with vigorous stirring. After 2.6 liters of saturated diammonium tartrate solution had been added, the mixture was stirred for two hours. Next, the (lighter) tetrahydrofuran solution was separated and concentrated by evaporation in vacuo. The aqueous solution was extracted twice, each time with 400 ml of methylene chloride. The evaporation residue of the tetrahydrofuran phase was dissolved with the methylene chloride extracts, and the solution was washed twice, each time with 400 ml of water, dried with sodium sulfate, and concentrated by evaporation in vacuo. The residue (69 gm) consisted of the ethylene ketal of N-(2-methoxyethyl)-noroxymorphone, which was subjected to the ketal splitting described below without purification.

(c) N-(2-methoxyethyl)-noroxymorphone hydrochloride

For the ketal splitting, the residue from step (b) was refluxed for one hour with a mixture of 70 ml of water and 40 ml of conc. HCl. The resulting clear brown solution was cooled and mixed with 800 ml of acetone. N-(2-methoxyethyl)-noroxymorphone hydrochloride crystallized out. After the mixture was left to stand overnight in a refrigerator, it was subjected to suction filtration, washed with acetone, and dried at 60° C. Seventy-four grams (70.7% of theory) of N-(2-methoxyethyl)-noroxymorphone hydrochloride, melting point 205° C., were obtained. After recrystallization from 167 ml of water (in which it was dissolved at boiling temperature) and 1.4 liters of acetone (added after the aqueous solution had cooled to 50° C.), 62.0 gm of pure substance with a melting point of 265° to 267° C. were obtained. The analytically pure substance obtained by further recrystallization from methanol melted at 269° to 270° C.

The following examples illustrate a few pharmaceutical compositions comprising one of the compounds of Formula I as active substance and represent the best modes contemplated of using the invention.

EXAMPLE 3

Tablets Containing 20 mg of Active Substance

Each tablet has the following composition:

| Component | Amount (mg) |
|---|---|
| Active substance | 20.0 |
| Lactose | 120.0 |
| Corn starch | 50.0 |
| Colloidal silicic acid | 2.0 |
| Soluble starch | 5.0 |
| Magnesium stearate | 3.0 |
| Total: | 200.0 |

The active substance is mixed with some of the excipients and granulated with a solution of the soluble starch in water. After the granulate has dried, the remaining excipients are added, and the mixture is compressed to form tablets.

EXAMPLE 4

Coated Tablets Containing 15 mg of Active Substance

Each tablet core has the following composition:

| Component | Amount (mg) |
|---|---|
| Active substance | 15.0 |
| Lactose | 100.0 |
| Corn starch | 95.0 |
| Colloidal silicic acid | 2.0 |
| Soluble starch | 5.0 |
| Magnesium stearate | 3.0 |
| Total: | 220.0 |

Preparation

The active substance and excipients are compressed to form tablet cores as described in Example 3, and these cores are coated with sugar, talc, and gum arabic in conventional manner.

EXAMPLE 5

Suppositories Containing 10 mg of Active Substance

Each suppository has the following composition:

| Component | Amount (mg) |
|---|---|
| Active substance | 10.0 |
| Lactose | 150.0 |
| Suppository mass (e.g., WITEPSOL ® H19 or W45, available from Chemische Werke Witten GmbH) | 1540 |
| Total: | 1700 |

Preparation

The active substance and lactose are mixed together, and the mixture is uniformly suspended in the molten suppository mass. The suspensions are poured into chilled molds to form suppositories weighing 1.7 gm each.

EXAMPLE 6

Ampules Containing 1 mg/ml of Active Substance

Each ampule has the following composition:

| Component | Amount |
|---|---|
| Active substance | 1.0 mg |
| Sodium chloride | 10.0 mg |
| Doubly distilled water q.s. ad | 1.0 ml |

Preparation

The active substance and sodium chloride are dissolved in doubly distilled water, and the solution is transferred under sterile conditions into ampules.

EXAMPLE 7

Drops Containing 7 mg/ml of Active Substance

One hundred milliliters of suspension has the following composition:

| Component | Amount |
|---|---|
| Active substance | 700 mg |
| Methyl p-hydroxybenzoate | 70 mg |
| Propyl p-hydroxybenzoate | 30 mg |
| Demineralized water q.s. ad | 100.00 ml |

Preparation

The active substance and preservatives are dissolved in demineralized water, and the solution is filtered and transferred into vials each containing 100 ml.

The preceding specific embodiments are illustrative of the practice of the invention. It is to be understood, however, that other excipients known to those skilled in the art or disclosed herein, may be employed without departing from the spirit of the invention or the scope of the appended claims.

We claim:

1. N-(2-Methoxyethyl)-noroxymorphone or a pharmacologically acceptable acid addition salt with an inorganic or organic acid.

2. A pharmaceutical composition for relieving pain which comprises a pain-relieving effective amount of one or more compounds of claim 1 and conventional inert carrier and/or diluent.

3. A process of relieving pain in a warm-blooded host in need of such relief with comprises perorally, parenterally, or rectally administering to said host an effective pain-relieving amount of a compound of claim 1.

* * * * *